United States Patent
Godoy et al.

(10) Patent No.: US 6,950,004 B2
(45) Date of Patent: Sep. 27, 2005

(54) QUADRILATERAL ELECTROMAGNETIC COIL ASSEMBLY

(76) Inventors: Arthur Alexander Godoy, 205 Santa Ana Ave., Long Beach, CA (US) 90803; Stephen Andrew Godoy, 205 Santa Ana Ave., Long Beach, CA (US) 90803

( * ) Notice: Subject to any disclaimer, the term of this patent is extended or adjusted under 35 U.S.C. 154(b) by 104 days.

(21) Appl. No.: 09/953,312

(22) Filed: Nov. 26, 2001

(65) Prior Publication Data

US 2002/0050884 A1 May 2, 2002

Related U.S. Application Data

(60) Provisional application No. 60/233,778, filed on Sep. 19, 2000.

(51) Int. Cl.[7] ................................................. B43K 5/00
(52) U.S. Cl. ...................................... 336/160; 81/9.22
(58) Field of Search ................................ 336/160, 198, 336/212, 165, 208, 192; 81/9.22, 438; 335/210

(56) References Cited

U.S. PATENT DOCUMENTS

| | | | | |
|---|---|---|---|---|
| 4,159,659 A | * | 7/1979 | Nightingale | 81/9.22 |
| 4,216,455 A | * | 8/1980 | Hester | 336/160 |
| 4,397,234 A | * | 8/1983 | Lee et al. | 101/93.29 |
| 4,587,501 A | * | 5/1986 | Agatahama et al. | 335/80 |
| 4,626,813 A | * | 12/1986 | Koga et al. | 335/278 |
| 4,639,706 A | * | 1/1987 | Shimizu | 336/170 |
| 5,038,123 A | * | 8/1991 | Brandon | 335/128 |
| 5,138,295 A | * | 8/1992 | Larson et al. | 336/160 |
| 5,289,144 A | * | 2/1994 | Liao | 335/78 |
| 5,293,146 A | * | 3/1994 | Aosaki et al. | 336/206 |
| 5,400,006 A | * | 3/1995 | Cardozo | 336/175 |
| 5,401,242 A | * | 3/1995 | Yacowitz | 604/48 |
| 5,504,469 A | * | 4/1996 | McGrane | 336/206 |
| 5,600,294 A | * | 2/1997 | Buenconsejo et al. | 336/192 |
| 6,550,356 B1 | * | 4/2003 | Underwood | 81/9.22 |
| 6,596,007 B2 | * | 7/2003 | Evans | 606/186 |

* cited by examiner

Primary Examiner—Anh Mai
(74) Attorney, Agent, or Firm—Miller Nash LLP

(57) ABSTRACT

Prior art electromagnetic coil technology in tattoo machines employs a round steel post to alternately repel and attract an armature bar retained by a spring, reciprocally moving a needle bar and attached needle groupings into and out of the skin in the act of tattooing. The present invention uses a hexahedron shaped steel post to increase the surface area contacted on the armature bar, improving the magnetism and general movement of the bar. The improved rate of movement of the armature improves the overall functioning of the tattoo machine including the operator's ability to achieve more solid color, smoother shading, and more consistent lines. Removable retaining washers and o-rings are employed to allow the operator to customize and repair the magnetic wire.

30 Claims, 5 Drawing Sheets

QUADRILATERAL ELECTROMAGNETIC COIL ASSEMBLY

This application is cont. of Provisional Application 60/233,778 filed Sep. 19, 2000.

TECHNICAL FIELD

This invention relates generally to the field of tattooing and tattoo machines. More particularly, the invention relates to an apparatus for maximizing the efficiency of the electromagnetic coils employed in tattoo machines to reciprocate the tattoo needle assembly.

BACKGROUND OF THE INVENTION

This invention pertains to the field of tattooing, and is intended to improve the coil technology currently used in tattoo machines. The electromagnetic coil assembly is the most important component of any tattoo machine that employs electromagnetism to reciprocate the needle assembly. Prior art tattoo machines employ electromagnetic coils with a cylindrical steel core wrapped in copper wire (typically American wire gage ("awg") 24) through which AC current is passed to create an electromagnet. The alternating polarity of the electromagnet alternately attracts and repels an armature bar at a high rate of reciprocation. A tattoo needle assembly is attached to the reciprocating armature bar. The tattoo needle is then used to intradermally inject ink into a human or animal subject. Prior art coils use non-removable retaining washers and o-rings to retain the wires.

It is an object of the present invention to provide a coil core which maximizes the contact area between the core and the armature bar in order to maximize the efficiency and power of the electromagnet. It is a further object of the present invention to provide a coil assembly which can be easily maintained and customized by the end user.

SUMMARY OF THE INVENTION

It is the object of the present invention to provide an improved electromagnetic coil assembly which overcomes the disadvantages of the prior art by optimizing the reciprocation of the needle in a tattoo machine and facilitates the removal and replacement of the retaining washers and o-rings.

It is also an object of the present invention to provide a quadrilateral cross-section post or core, thereby increasing the surface area where the posts contact the armature bar and thereby improving the magnetism of the coil. In accordance with the present invention, an apparatus for an improved electromagnetic coil in a tattoo machine is provided. The coil comprises a quadrilateral cross section core with wire wound around the core. The coil may further comprise retaining means proximate to each end of the core seated in circumferential grooves. Insulating tape may be inserted between the core and the wire. The retaining means may be nylon or plastic washers held in place by o-rings seated in the chamfered edges of the grooves. 21 or 23 awg wire may be used, and a capacitor to regulate the current.

An electromagnetic coil assembly with a hexahedron steel core, wire wound around the core, and a reciprocating armature bar is also disclosed. The coil assembly may include retaining washers retained by o-rings.

The coil assembly may be modular with removable parts such that the end user may customize the layers of wound wire to create a level of electromagnetism as desired, or to repair the coil.

The coil assembly may be provided in a kit format and assembled by the end user.

BRIEF DESCRIPTION OF THE DRAWINGS

The apparatus and method of the present invention will now be described with reference to the accompanying drawing figures, in which.

DETAILED DESCRIPTION AND PREFERRED EMBODIMENT

Figure 1:
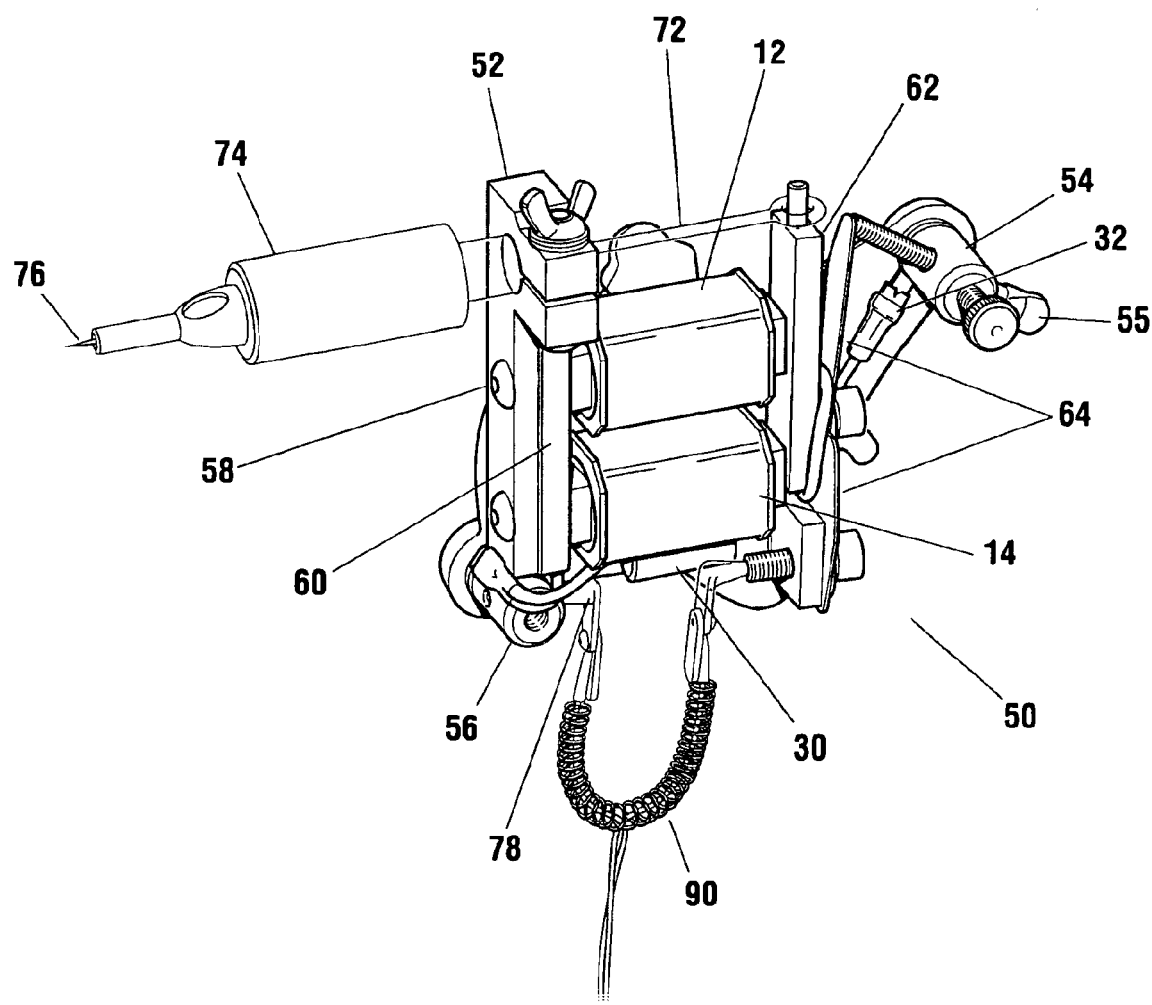
FIG. 1 is a perspective view of a tattoo machine with square electromagnetic coil assemblies according to the invention.

FIG. 1 depicts the preferred embodiment of the square electromagnetic coil assembly 10 in a standard tattoo machine 50 in accordance with the present invention. Tattoo machines 50 are generally comprised of a frame 52, typically made of metal. Standard frames 52 have a lower binding post 56 and an upper binding post 54. There is also typically a coil mounting bracket or yoke 60 at the front portion of the frame 52, and a pair of springs 64 at the rear portion of the frame 52. At least one electromagnetic coil 10 is mounted on the yoke 60. Preferably there are two coils, a front coil 12 and back coil 14. An armature bar 62 is attached to a spring 64 which extends from the frame 52 and is adapted to reciprocate when AC power is applied to the electromagnetic coils 12 and 14 such that the armature bar 62 is alternately attracted by the coils 12 and 14, then retracted by a spring 64, as is known in the art. A power cord 80 brings the AC power to the coils 12, 14 and a capacitor 30.

Also as is known in the art, a needle bar 72 is attached to the armature bar 62. The needle bar 72 has a needle grouping 76 attached to the needle bar tip. A hollow housing or tube grip 73 is placed over the needle bar 72 to guide the reciprocating needle bar 72. The present invention relates generally to the coil 10.

Figure 2:
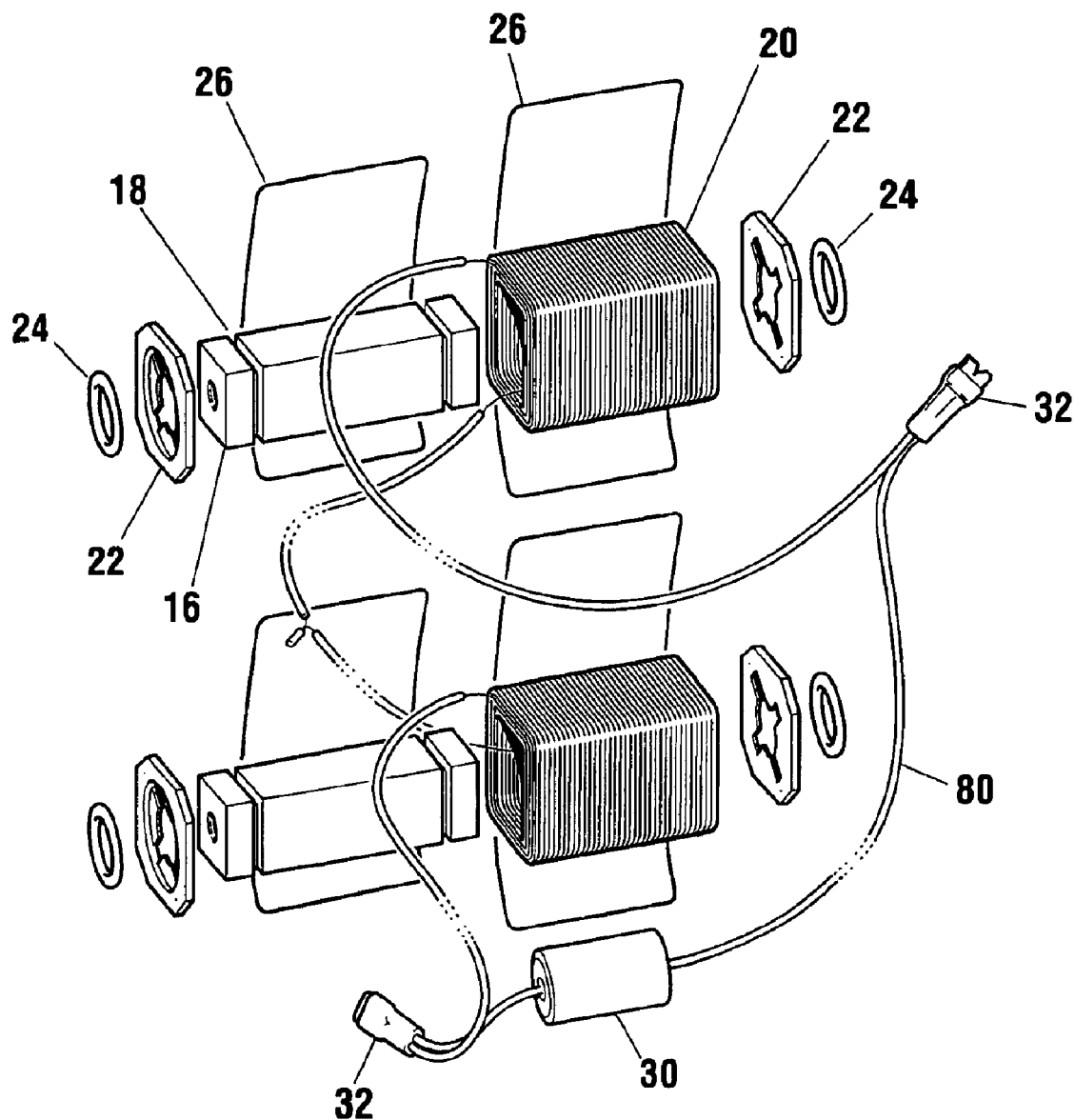
FIG. 2 is an exploded perspective view of a dual square electromagnetic coil assembly according to the invention.

Referring now to FIG. 2, the quadrilateral electromagnetic coil bobbin assembly has a core 16 which is a hexahedron shaped post which has a square cross section in the preferred embodiment. The core 16 is optimally made of metal such as iron or steel, and is preferably made of 1018 to 1025 grade steel. The core 16 has a circumferential groove 18 located proximal to each end. The groove 18 has chamfered edges. The core 16 has a threaded hole 34 in the bottom end adapted to accept a retaining screw (not shown). A retaining washer 22 (preferably a flexible nylon washer) seats in each groove 18.

An o-ring 24 (preferably a nitrile-butadene rubber ("buna-n") o-ring) abuts the distal side of each washer 22 thereby retaining it in place on the core 16. Protective tape 26, preferably 1 mil. polyimide insulation tape, is wrapped around the core 16 between each of the washers 22 to stop the passage of electrical current. The assembled core 16, washers 22, o-rings 24, and tape 26 is called a bobbin 36. The lower washer 22 has two holes (not shown) disposed in it, through which a copper wire 20 is inserted. The wire 20 is optimally between awg 22 and 25, and is preferably awg 21 or awg 23 magnetic copper wire 20, which advantageously allows a higher current than in prior art awg 24 coils 10 to flow, thereby creating greater electromagnetism and a more accurate, efficient and powerfull tattoo machine 50.

In the preferred embodiment there are two coils 10, a front coil 12 located proximal to the needle bar 72 and a back coil 14 located on the frame 52 distally to the needle bar 72. In the front coil 12 the wire 20 is wound around the core 16 to create layers of wire 20. For the front coil 12, between 4 and 11 layers of wire 20 are optimal. For a back coil 14, between 4 and 10 layers are optimal. The back coil 14 preferably has an even number of layers. The front coil 12 preferably has one more layer of wire 20 than the back coil 14. The wire 20 is inserted through the lower washer 22, wound about the core 16, then exits through the second hole (not shown) in the lower washer 22 if the number of winds is even. If the number of winds or layers around the core 16 is odd, then the wire 20 exits the bobbin 36 through a hole 34 in the top washer 22. In the preferred embodiment an electrolytic axial capacitor 30 is inserted in parallel with the coils 12, 14. The wire 20 is then wrapped in insulating tape 26. Decorative or branded stickers (not shown) may be applied to the tape 26 for aesthetic, marking or advertising purposes. All visible wires 20 must be shrink-wrapped or otherwise insulated. The retaining washers 22 secure the wire 20 into layers and form the top and bottom of the bobbin 36.

When used with the electromagnetic coil 10, the armature bar 62 powers a needle bar 72 and attached needle groupings 76 that move into and out of the skin during tattooing. Increasing the amount of metal-to-metal contact results in significant improvements in the overall functioning of the tattoo machine 50 and the operator's ability to achieve more solid color, smoother shading, and more consistent lines, all of which depend on the rate of movement of the armature bar 62.

Figure 3:
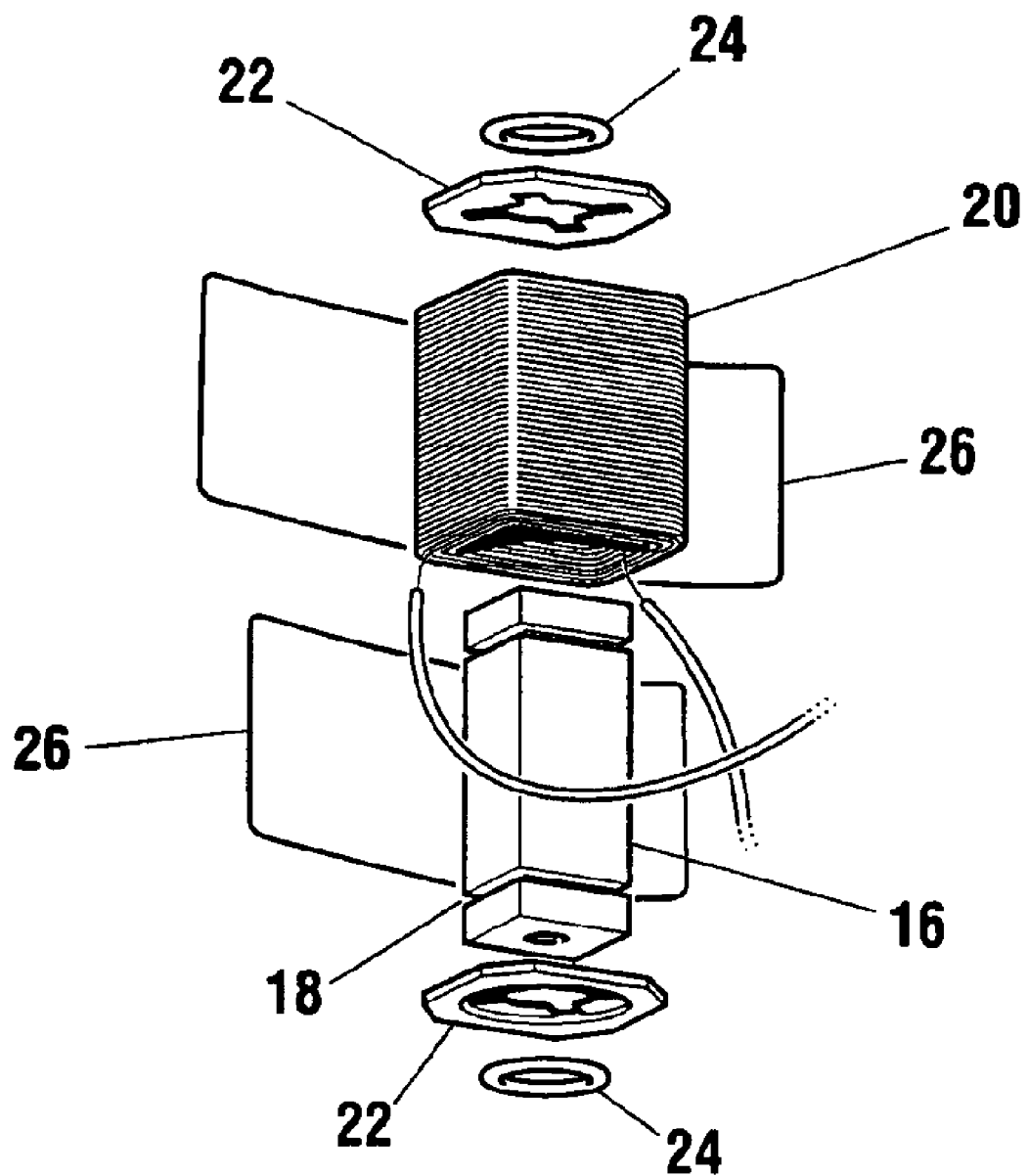
FIG. 3 is an exploded perspective view of a single square electromagnetic coil assembly according to the invention.

Referring now to FIG. 3, an exploded perspective view of a square electromagnetic coil bobbin assembly 10 is shown. The core 16 may be machined on a CNC mill from metal which is able to be magnetized, such as iron or steel. In the preferred embodiment, a piece of 1018 to 1025 grade steel stock is machined according to specifications to form a shape that appears rectangular when viewed from the side and square when viewed from the top. Grooves 18, preferably measuring 1/16" by 1/16" are machined completely around the rectangular prism steel post or core 16, 1/8" down from the top and 1/8" up from the bottom, so that the grooves 18 are parallel with the ends of core 16. Chamfered edges are machined on the edges of the machined grooves 18. The chamfered edges serve as a seat to snugly receive the washer 22 and o-ring 24. A hole 34 is drilled and tapped into the center of the bottom end of the core 16 to a penetration depth of between 1/4" and 1/2" (recommended taps are 8–32 or 6–32). A layer of polyimide insulation tape 26 is wrapped completely around the core 16 so that it covers all four sides of the core 16 between the machined grooves, including the chamfered edges. Retaining washers 22, preferably plastic and measuring approximately 1" in diameter and 1–16" in thickness are placed in the grooves 18 at the top and bottom of the core 16. Three holes are drilled in each of the two retaining washers 22: one larger hole 34 in the center, measuring at least 1/4" in diameter; and two other smaller holes 34 close to the outer edge of the washer and measuring at least 1/32" in diameter. Each retaining washer 22 is secured with an o-ring 24 inserted on top of the retaining washers 22 under the edges of the machined grooves 18.

The steel core 16 with polyimide tape 26, retaining washers 22, and o-rings 24 (together referred to as a bobbin) is wound in magnetic copper wire 20 in the area between the retaining washers 22, much like thread is wound around a bobbin in a sewing machine. The length of the wire 20 will vary depending on the size of the area to be wound, the thickness of the core 16, and the number of layers to be wound around the core 16. If used as the front bobbin 36, the coil 12 may have between 4 and 11 layers of wire 20, and the back coil 14 may have between 4 and 10 layers (the back coil 14 must have an even number of layers). The wire starts from the small hole 34 near the inner edge of the retaining washer 22 and winds onto the polyimide insulation tape 26 in layers from the bottom to the top and then back to the bottom, and so on until the desired number of layers is attained. The wire 20 exits through the small hole 34 near the outer edge of the retaining washer 22 at one or the other end of the core 16, depending on whether an odd or even number of wire layers is used.

Any form of tape 26 is wrapped around the exterior of the magnetic copper wire 20 to protect it. The ends of the wire 20 will protrude from the smaller inner and outer holes 34 in the retaining washers 22. A decal printed with the company logo may be applied for aesthetic purposes.

Figure 4:
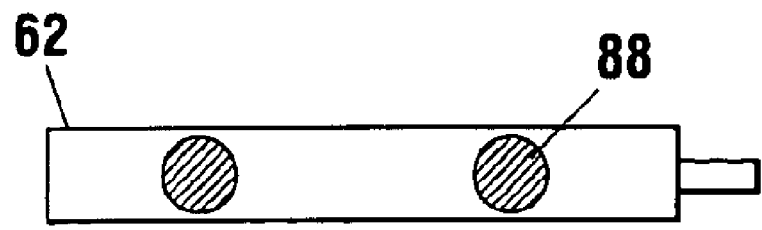
FIG. 4 is a plan view of the contact area of prior art coil assemblies on an armature bar.

Referring now to FIG. 4, a plan view of the armature bar 62 is shown. The shaded area 88 indicates the area contacted by the ends of the core 16 of each coil 10 in a prior art tattoo machine 50 having a front coil 12 and back coil 14.

Figure 5:
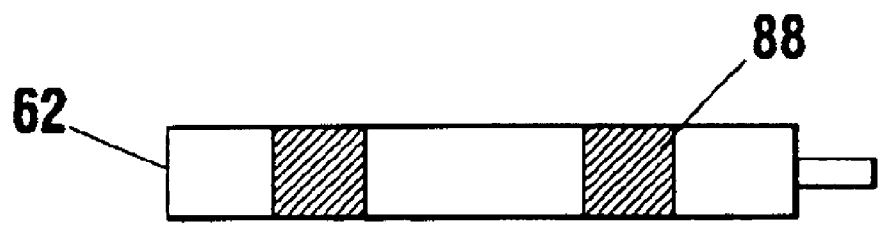
FIG. 5 is a plan view of the contact area of square electromagnetic coil assemblies on an armature bar according to the invention.

FIG. 5 shows the shaded area 88 on the armature bar 62 where the ends of the cores 16 will contact in the preferred embodiment also having a front coil 12 and a back coil 14.

Figure 6:
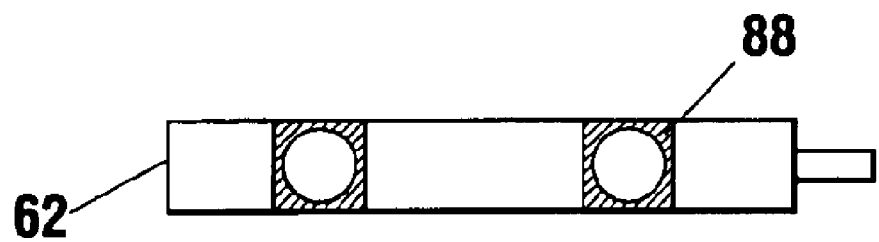
FIG. 6 is a plan view comparing both the prior art and present invention contact areas of a coil assembly on an armature bar.
Figure 7:
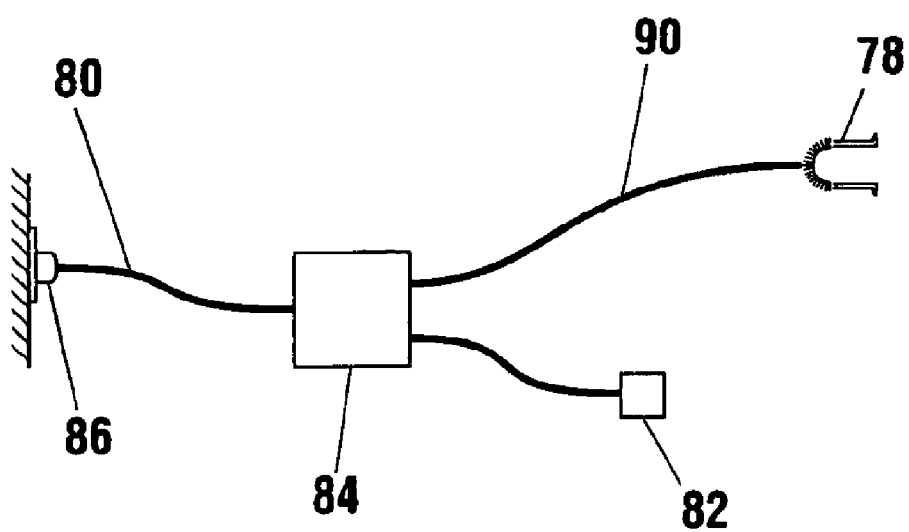
FIG. 7 is a schematic of a power supply according to the invention.

FIG. 6 shows the shaded area 88 indicating the increased surface contact area between the armature bar 62 and coils 12, 14 provided by the present invention. Referring now to FIG. 7, electrical current is delivered to the square electromagnetic coil bobbin assembly 10 from an external power source 86 (either a 110V to 220V wall socket). Current flows from the external source 86 through a cord 28 to an adjustable power supply 84 that is controlled by depressing a footswitch 82, then from the power supply 84 to the tattoo machine 50 through a clip cord wire 90 (or alternatively an RCA jack system) to the lower binding post 56 (see FIG. 1). Now referring again to FIG. 1, from the lower binding post 56, the current passes through two wires 80, one attached to an electrolytic axial capacitor 30 and the other attached to the back coil 14. The current passes through the back coil 14 to the front coil 12 through the wire 80 that joins the front coil 12 and back coil 14, and simultaneously through the electrolytic axial capacitor 30.

The current then passes out through ending wires 80, one from the front coil 12 and the other from the electrolytic axial capacitor 30, which join at the upper binding post assembly 54. When current is delivered to a pair of coils 10, it passes through the magnetic copper wire 20 that winds around the square steel posts or cores 16, magnetizing both of the steel cores 16. Once magnetized, the cores 16 function as magnets with alternating polarity, attracting the armature bar 62 with the aid of resistance from a pair of steel springs 64, which act to retract the armature bar 62 when the coils 10 are demagnetized. The attracting of the armature bar 62 results in the reciprocating motion of the armature bar 61 (similar to the motion of a sewing machine needle) and the attached needle bar 72.

The electrolytic axial capacitor 30 works with the coil assembly 10 to store and release the electrical charges that pass through the assembly, smoothing and regulating current flow. Magnetism is strengthened or reduced using an adjustable electrical power supply 84.

The coil assembly 10 may be used in other electromechanical devices where an electromagnetic coil 10 is required.

The preferred embodiments herein described are not intended to be exhaustive or to limit the scope of the invention to the precise forms disclosed. They are chosen and described to best explain the principles of the invention and its application and practical use to allow others skilled in the art to comprehend its teachings.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. In a tattoo machine having a frame, an armature bar, at least one coil assembly comprising:
   a) an elongated steel core having a quadrilateral cross section; and
   b) at least one wire wound directly around said core, whereby said armature bar is adapted to be displaced by said coil assembly upon passage of a current through said coil assembly.

2. A coil assembly as in claim 1 further comprising a retaining means at each end of said core adapted to contain said wire.

3. A coil assembly as in claim 2 wherein said core is a square in cross section.

4. A coil assembly as in claim 3 wherein said core has a circumferential, transverse groove proximal to each longitudinal end.

5. A coil assembly as in claim 4 wherein said retaining means is a removable washer seated in each said groove, thereby retaining said wire on said core between said washers.

6. A coil assembly as in claim 5 further comprising insulating tape between said wire and said core.

7. A coil assembly as in claim 6 wherein said tape is polyimide insulation tape.

8. A coil assembly as in claim 6 further comprising an o-ring abutting at least one face of each said washer thereby removably retaining said washer in said groove on said core.

9. A coil assembly as in claim 1 wherein said wire is one of American wire gage 21 and 23 magnetic copper wire thereby allowing passage of a high current through said coil assembly.

10. A coil assembly as in claim 1 further comprising a capacitor in parallel with said coil such that said current is regulated.

11. An electromagnetic coil assembly comprising a rectangular prism steel core having an active and an inactive end, at least one wire wound around said core, and an armature bar adapted to reciprocate against the active end of said core.

12. The coil assembly of claim 11 further comprising a retaining washer at each end of said core adapted to retain said wire in place.

13. The coil assembly of claim 12 further comprising at least one groove in said core proximal to each end adapted to receive said washers.

14. The coil assembly of claim 13 further comprising at least one o-ring abutting a distal face of said washers thereby retaining said washers in place.

15. The coil assembly of claim 14 further comprising insulating tape between said core and said wire, and around said wire.

16. The coil assembly of claim 11 wherein said wire is one of American wire gage 21 or 23.

17. In a tattoo machine having a frame, an armature bar, at least one electromagnetic coil comprising:
   a) an elongated steel core having a quadrilateral cross section and two longitudinal ends;
   b) at least one circumferential, transverse grooves proximal to a longitudinal end of said core; and
   c) at least one wire wound directly around said core.

18. A coil assembly as in claim 17 wherein there are at least two said grooves, and at least one said grooves is disposed at an opposite longitudinal end of said core.

19. A coil assembly as in claim 17 further comprising a retaining means disposed at each longitudinal end of said core adapted to contain said wire.

20. A coil assembly as in claim 19 wherein said retaining means is a removable washer seated in each said groove, thereby retaining said wire on said core between said washers.

21. A coil assembly as in claim 20 further comprising an o-ring abutting at least one face of each said washer thereby removably retaining said washer in said groove on said core.

22. A coil assembly as in claim 20 further comprising insulating tape between said wire and said core.

23. A coil assembly as in claim 22 wherein said tape is polyimide insulation tape.

24. In a tattoo machine having a frame, a reciprocating needle, and an armature bar, at least one coil assembly comprising
   a) an elongated steel core having a quadrilateral cross section and two ends;
   b) at least one wire wound directly around said core;
   c) a retaining means at each end of said core adapted to retain said wire; and
   d) at least two circumferential, transverse grooves proximal to each said end of said core, such that upon passage of current through said coil assembly said armature bar reciprocates thereby reciprocating said needle.

25. A coil assembly as in claim 24 wherein a plurality of said grooves are at each end of said core.

26. A coil assembly as in claim 24 wherein a plurality of said grooves are at each end of said core.

27. A coil assembly as in claim 24 wherein said retaining means is a removable washer seated in each said groove, thereby retaining said wire on said core between said washers.

28. An electromagnetic coil assembly and reciprocating armature, said coil assembly comprising an elongated metal core having a quadrilateral cross-section, and an active end, said armature bar having an interior face with a quadrilateral surface area, said core and said armature bar adapted to maximize the contact area between said active end of said core and said interior face of said armature bar.

29. A coil assembly as in claim 28 wherein at least one wire of heavy gage is wound around said core such that high voltage electrical current can pass therethrough.

30. In a new tattoo machine having a frame and a reciprocating needle, and an armature bar adapted to reciprocate said needle upon passage of current through a coil assembly, said coil assembly comprising:

a) an elongated steel core having a quadrilateral cross section;

b) at least two circumferential, transverse grooves proximal to each longitudinal end of said core;

c) at least one wire wound directly around said core; and d) a retaining washer at each end of said core adapted to retain said wire in place.

* * * * *